(12) United States Patent
Kim et al.

(10) Patent No.: US 9,370,504 B2
(45) Date of Patent: Jun. 21, 2016

(54) PHARMACEUTICAL COMPOSITION CONTAINING 1,2-DITHIOLTHIONE DERIVATIVE FOR PREVENTING OR TREATING DISEASE CAUSED BY OVEREXPRESSION OF LXR-α

(75) Inventors: Sang Geon Kim, Seoul (KR); Sung Hwan Ki, Seoul (KR); Seong Hwan Hwang, Ulsan (KR)

(73) Assignee: SNU R&DB FOUNDATION, Seoul (KR)

( * ) Notice: Subject to any disclaimer, the term of this patent is extended or adjusted under 35 U.S.C. 154(b) by 250 days.

(21) Appl. No.: 13/057,401

(22) PCT Filed: Jul. 30, 2009

(86) PCT No.: PCT/KR2009/004242
§ 371 (c)(1),
(2), (4) Date: Feb. 3, 2011

(87) PCT Pub. No.: WO2010/016681
PCT Pub. Date: Feb. 11, 2010

(65) Prior Publication Data
US 2011/0152524 A1 Jun. 23, 2011

(30) Foreign Application Priority Data
Aug. 4, 2008 (KR) .................. 10-2008-0075994

(51) Int. Cl.
*A61K 31/385* (2006.01)
(52) U.S. Cl.
CPC .................... *A61K 31/385* (2013.01)
(58) Field of Classification Search
None
See application file for complete search history.

(56) References Cited

U.S. PATENT DOCUMENTS

2003/0191137 A1* 10/2003 Kim et al. ............... 514/255.05

FOREIGN PATENT DOCUMENTS

| CN | 1625399 A | 6/2005 |
|---|---|---|
| EP | 1593673 A1 | 11/2005 |
| JP | 7-112978 A | 5/1995 |
| JP | 1995-112978 * | 5/1995 |
| KR | 1020050100787 A | 10/2005 |
| KR | 10-2006-0031952 A | 4/2006 |
| KR | 10-0576157 B1 | 4/2006 |
| RU | 10-0576157 | 4/2006 |
| RU | 2292043 C2 | 1/2007 |
| RU | 2305840 A | 6/2007 |
| WO | WO 94/16563 * | 8/1994 |
| WO | 03/020711 A1 | 3/2003 |
| WO | 03/066058 A1 | 8/2003 |
| WO | 2005/046689 A2 | 5/2005 |
| WO | 2005/051941 A1 | 6/2005 |
| WO | 2006/080745 A1 | 8/2006 |
| WO | WO 2007/094632 A1 | 8/2007 |

OTHER PUBLICATIONS

Horton et al. "SREBPs: activators of the complete program of cholesterol and fatty acid synthesis in the liver", J Clin Invest. 2002;109(9):1125-1131.*
El-Bassiouni et al. "In vitro effect of low concentrations of oltipraz on the antioxidant defence of mouse hepatocytes and Schistosoma mansoni worms," Br J Biomed Sci. 2004;61(1):15-21 (abstract only).*
Farrell et al., "Nonalcoholic Fatty Liver Disease: From Steatosis to Cirrhosis," Hepatology vol. 43, Issue S1, pp. S99-S112, Feb. 2006.*
STN Record of KR 2006031956, citation date of 2006 (herein identified as STN Record of Kim et al.).*
www.cancer.org/acs/groups/cid/documents/webcontent/002043-pdf.pdf, downloaded Sep. 27, 2014.*
English Translation of Kim (English translation of KR 2006031956, published Apr. 14, 2004).*
Corton, Christopher J., et al. "Mimetics of Caloric Restriction Induce Agonists of Lipid-activated Nuclear Receptors." *The Journal of Biological Chemistry*. vol. 279, No. 44, Issue of Oct. 29, 2004. pp. 46204-46212.
Vincenzo O. Palmieri et al., "Systemic Oxidative Alterations are Associated with Visceral Adiposity and Liver Steatosis in Patients with Metabolic Syndrome", The Journal of Nutrition, Dec. 2006, pp. 3022-3026, vol. 136, No. 12.
Russian Patent Office, Office Action issued on Mar. 1, 2012 in a counterpart Russian Application No. 2011108359.
European Patent Office, European Search Report issued in corresponding EP Application No. 09805142.8, dated Oct. 18, 2011.
People's Republic of China Patent Office, Office Action issued on Jan. 30, 2012 in a counterpart Chinese Application No. 200980130358.3.
Japan Patent Office, Office Action issued on Dec. 11, 2012 in Japanese Application No. 2011-520000.
European Patent Office, Office Action issued on Oct. 26, 2012 in a counterpart European Application No. 09 805 142.8.
Russian Patent Office, Office Action issued on Aug. 27, 2012 in Russian Application No. 2011108359.
D.A. Kharkevich, "Farmakolociva" [Pharmacology], Manual for students of medical institutes, Moscow, Meditsina, 1987, p. 47-48.
V. G. Belikov, [pharmaceutical Chemistry], 1993, vol. 1, pp. 43-47.

* cited by examiner

*Primary Examiner* — Jeffrey S Lundgren
*Assistant Examiner* — William Lee
(74) *Attorney, Agent, or Firm* — Sughrue Mion, PLLC

(57) ABSTRACT

Provided is a pharmaceutical composition that contains a 1,2-dithiolthionederivative, and is effective to prevent and treat a disease caused by overactivity of a liver X receptorα (LXRα) or a sterol response element binding protein (SREBP-1). Specifically, the pharmaceutical composition includes 1,2-dithiolthione derivatives such as 4-methyl-5-(2-pyrazinyl)-1,2-dithiol-3-thione, 3-methyl-1,2-dithiol-3-thione, or 5-(6-methoxypyrazinyl)-4-methyl-1,2-dithiol-3-thione. The pharmaceutical composition is effective for preventing and treating hypertension caused by renin, aldosteronism, adrenoleukodystrophy, glomerulosclerosis, proteinuria, nephropathy, liver steatosis, hypertriglyceridemia or hyperreninemia.

8 Claims, 8 Drawing Sheets
(1 of 8 Drawing Sheet(s) Filed in Color)

Oil Red O

ND + Vehicle

HFD + Vehicle

HFD + Oltipraz (10 mg/kg)

HFD + Oltipraz (30 mg/kg)

PHARMACEUTICAL COMPOSITION CONTAINING 1,2-DITHIOLTHIONE DERIVATIVE FOR PREVENTING OR TREATING DISEASE CAUSED BY OVEREXPRESSION OF LXR-α

TECHNICAL FIELD

The present invention relates to a 1,2-dithiolthione derivative for inhibiting the expression or activity of a liver X receptor α (LXRα) and the expression or activity of a sterol response element binding protein-1 (SREBP-1). The present invention also relates to a pharmaceutical composition including the 1,2-dithiolthione derivative. The pharmaceutical composition is effective for preventing and treating diseases caused by overexpression of LXRα or SREBP-1. Such diseases may include liver steatosis, hypertriglyceridemia, hyperreninemia, hypertension caused by renin, aldosteronism, adrenoleukodystrophy, glomerulosclerosis, proteinuria, and nephropathy.

The present invention is the culmination of a research project supported by the Engineering Research Center (ERC) of the Ministry of Education, Science, and Technology [Project No. R11-2007-107-01001-0, Research for metabolic and inflammatory].

BACKGROUND ART

A liver X receptor (LXR), a peroxisome proliferator-activated receptor (PPAR), and a farnesoid X receptor (FXR) are nuclear hormone receptors that belong to a Type II receptor superfamily. These receptors form a heterodimer together with a retinoid X receptor (RXR) and bind to DNA. When a ligand does not bind, the heterodimer binds to DNA and forms a complex together with a corepressor protein; on the other hand, when a ligand binds, a structural change occurs and the corepressor protein is separated and a coactivator protein binds, thereby promoting transcription of a target gene [Hermanson et al., *Trends Endocrinol. Metab.*, 2002, 13: 55-60]. Among nuclear hormone receptors, LXR plays an important role in controlling transcription of a gene that is related to cholesterol metabolism and homeostasis. Examples of such a gene include apolipoprotein E(apoE), ABCA1, ABCG1, ABCG5, ABCG8, cholesterol 7α-hydroxylase, and scavenger receptor Class B Type I [Schwartz et al., *Biochem. Biophys. Res. Commun.*, 2000, 274: 794-802]. In addition, LXR directly affects the SREBP-1c gene and controls lipid metabolism [Yoshikawa et al., *Mol. Cell. Biol.*, 2001, 21: 2991-3000].

LXR has two isomers including LXRα and LXRβ. In most case, LXRα exists in the liver, and LXRβ exists in most organs. LXRα is activated by oxysterols that are natural ligands, high glucose, and T0901017 and GW3965 that are artificial ligands, and controls the expression of genes that relate to lipid synthesis and cholesterol homeostasis. When lipids are produced in the liver, LXRα functions as a lipid sensor and significantly increases the expression and activity of SREBP-1c that is a key transcription factor for controlling expression of lipogenic genes and thus, promotes fatty acid synthesis in liver tissues and increases the amount of triglyceride in blood.

LXRα-induced non-alcoholic liver steatosis may be developed through two different pathways: a SREBP-1c-dependent pathway and a SREBP-1c-independent pathway. SREBP-1c-dependent liver steatosis is developed because lipogenic genes are more expressed through transcription activity of LXRα-mediated SREBP-1c. SREBP-1c-independent liver steatosis is developed because activity of LXRα leads to an increase in expression of a CD36 protein that is a carrier of free fatty acids and thus, more fatty acids are moved to the liver. As described above, the activity of LXRα promotes development of non-alcoholic liver steatosis. However, medicines that inhibit development of liver steatosis by controlling the activity of LXRα have not been developed.

SREBP is a protein that binds to a sterol response element (SRE) that is a transcription control site of a gene that is controlled by sterol, and exists in three isoforms: SREBP-1a, SREBP-1c, and SREBP-2. SREBP-1a and SREBP-1c are transcribed from the same gene, and SREBP-2 is expressed from a different gene. SREBP-1c is a transcription factor for controlling transcription of genes that relates to synthesis of fatty acids, and SREBP-2 is a transcription factor for controlling transcription of genes that relates to synthesis of cholesterol. In an resting condition, SREBP exists in endoplasmic reticulum membrane and the size thereof is 125 kDa. Before being activated by lack of sterol, SREBP binds to a membrane in an inactivated form. Then, when activated, SREBP moves to a Golgi body, and then is broken down into activated proteins having the size of 65 kDa. When activated, SREBP moves into a nucleus and binds to SRE of target genes and increases expression of lipid synthesis genes. Target genes of SREBP-1c are enzymes that promote fatty acid synthesis. Examples of such an enzyme include fatty acid synthase (FAS), acetyl CoA carboxylase (ACC), and stearoyl CoA desaturase (SCD). When the amount of free fatty acids that are moved from the blood into the liver and that are synthesized de novo in the liver is greater than the amount of fatty acids that are secreted into the form of very low density lipoprotein (VLDL) and that are β-oxidized, a lipid metabolism balance in the liver is broken and liver steatosis is developed. Thus, SREBP-1c that induces and controls FAS, ACC, and SCD proteins that promotes fatty acid synthesis is an important factor contributing to alcoholic or non-alcoholic liver steatosis [Kohijma et al., *Int. J. Mol. Med.*, 2008, 21(4): 507-511, Donohue, *World J. Gastroenterol.* 2007, 13(37): 4974-4978]. Liver steatosis refers to a disease state in which the fat content of the liver is 5% or more of the entire weight of the liver. Liver diseases including liver steatosis are the most common cause of death excluding cancers in adults between the ages of 40 and 50. In industrialized countries, about 30% of the respective populations have symptoms of liver steatosis, and 20% of the cases develop into liver cirrhosis through liver fibrosis. 50% of liver cirrhosis patients die of liver disease within 10 years of being diagnosed with liver cirrhosis. Cases of non-alcoholic liver steatosis are increased due to more westernized high lipid diets and lack of exercise. Currently, the only way of treating liver steatosis is to improve lifestyle factors such as diet.

There are almost no available medicines that are effective for treating liver steatosis, and only exercise and diets are recommended. However, the resultant treatment effects are too low. Thus, there is a need to develop drugs for effectively treating liver steatosis. Meanwhile, betaine, glucuronate, methionine, choline, lipotrophic preparations are used as drug supplement therapy, but medical or pharmaceutical effects of these materials have not been proved. Accordingly, there is a need to develop a drug for effectively treating liver steatosis without side effects.

Meanwhile, SREBP-1 and SREBP-2 are more expressed in kidneys in older people and due to the increased expression of SREBP-1 and SREBP-2, lipid synthesis and accumulation of triglyceride and cholesterol in kidneys are increased, which may cause glomerulosclerosis, proteinuria, and nephropathy [Jiang et al., *Kidney Int.*, 2005, 68(6): 2608-2620].

It is reported that LXRα plays an important role in secretion of renin in the kidney. LXRα and LXRβ all are sufficiently expressed in juxtaglomerular cells that generate renin. According to Morello et al., T0901017 and GW3965, which are agonists of LXRα, increase expression of mRNA of renin in the kidney, and renin activity in blood [Morello et al., *J. Clin. Invest.*, 2005, 115: 1913-1922]. When there is excessive renin in blood, hyperreninemia is developed and thus, hypertension and aldosteronism are developed.

LXR also controls expression of an ABCD2 gene that relates to adrenoleukodystrophy (ALD) and thus, an inhibitor of LXR is effective for treating ALD, wherein ALD is a rare disease caused when a very-long-chain fatty acid (VLCFA) in vivo is not decomposed and enters the brain and destroys nerve cells. [Weinhofer et al., *J. Biol. Chem.*, 2005, 280: 41243-41251].

Dithiolthiones are sulfur-containing compounds, and are found in Brassicaceae vegetables, and some substituents thereof have a liver protection effect. A representative compound of 1,2-dithiolthione is oltipraz(4-methyl-5-(2-pyrazinyl)-1,2-dithiol-3-thione) which was once used to treat schistosomiasis in the early 1980s and to develop a drug for cancer chemoprevention and a drug for treating liver cirrhosis. Oltipraz contributes to an increase in the content of thiol in cells of tissues in vivo, and induces, in addition to the expression of enzymes that relate to maintenance of glutathione (GSH) pool, the expression of enzymes that relate to detoxification of electrophilic materials. Examples of the enzymes whose activities are increased due to oltipraz include NAD(P)H: quinone reductase, microsomal epoxide hydrolase, glutathione S-transferase (GST), and UDP-GT. In particular, GST is an enzyme that prevents hepatotoxicity stemming from toxic materials such as tetrachloride or acetaminophen.

The inventors of the present invention found that oltipraz prevents expression of TGFβ and achieved a patent right to a pharmaceutical composition preventing and treating liver fibrosis and liver cirrhosis (KR No. 10-0404303.) The inventors of the present invention also found that oltipraz increases expression of C/EBPβ-LIP and inhibits expression of C/EBPα and PPARγ genes and achieved a patent right to a drug for preventing and treating obesity (KR No. 10-0576157). The inventors of the present invention also found that 1,2-dithiolthione compounds such as oltipraz enhance kinase activity of RSK1(p90 ribosomal S6 kinase 1) and achieved a patent right to a 1,2-dithiolthione-containing drug for preventing and treating diabetes and complications thereof (KR No. 10-0590818).

DISCLOSURE OF INVENTION

Technical Problem

The present invention provides inhibitors of LXRα or SREBP-1. The present invention also provides a pharmaceutical composition for preventing and treating a disease caused by overexpression of LXRα or SREBP-1.

Technical Solution

The inventors of the present invention screened effects of various drugs in order to solve the technical problems described above. As a result, they found that the expression and activity of LXRα and LXRα-dependent SREBP-1 are inhibited by administering drugs that contain 1,2-dithiolthione derivatives such as oltipraz. They also found that when SREBP-1 is inhibited by 1,2-dithiolthione derivative, expression of lipogenic genes that are target genes is substantially inhibited, and furthermore, high-lipid diet-induced triglyceride accumulation in liver tissue is inhibited. Based on the findings, the present invention provides a 1,2-dithiolthione derivative-containing pharmaceutical composition for preventing and treating a disease caused by overexpression of LXRα or SREBP-1.

Advantageous Effects

A pharmaceutical composition according to the present invention contains 1,2-dithiolthione derivatives as an effective component. The pharmaceutical composition is effective for preventing and treating a disease caused by the overexpression or overactivity of LXRα, or a disease caused by the overexpression or overactivity of SREBP-1. Examples of 1,2-dithiolthione derivatives include oltipraz(4-methyl-5-(2-pyrazinyl)-1,2-dithiol-3-thione), 3-methyl-1,2-dithiol-3-thione, and 5-(6-methoxypyrazinyl)-4-methyl-1,2-dithiol-3-thione. When the pharmaceutical composition is administered, the expression and activity of SREBP-1 are inhibited, wherein SREBP-1 is a key transcription factor that controls gene expression of lipogenic enzymes by adjusting activity of LXRα, and furthermore the expression of lipogenic genes is inhibited and thus, triglyceride accumulation in liver tissue, which occurs due to liver steatosis caused by metabolism disorder, is inhibited. Accordingly, pharmaceutical compositions containing the 1,2-dithiolthione derivatives as an effective component, according to the present invention, are effective for preventing and treating liver steatosis. Also, the pharmaceutical compositions are effective for preventing and treating hypertriglyceridemia, hyperreninemia, hypertension due to renin, aldosteronism, adrenoleukodystrophy, glomerulosclerosis, proteinuria, and nephropathy.

The present invention further provides a method for inhibiting the expression or activity of LXRα or SREBP-1 with the compound or composition provided herein. The inhibition may result in the prevention or treatment of a disease or condition associated with the over-expression or over-activity of LXRα or SREBP-1.

The present invention also provides a method for treating a disease or condition associated with the over-expression or over-activity of LXRα or SREBP-1, such as, for example, liver steatosis, hypertriglyceridemia, hyperreninemia, hypertension caused by renin, aldosteronism, adrenoleukodystrophy, glomerulosclerosis, proteinuria, and nephropathy, with compounds and compositions provided herein.

DESCRIPTION OF THE DRAWINGS

The file of this patent contains at least one drawing executed in color. Copies of this patent with color drawing(s) will be provided by the Patent and Trademark Office upon request and payment of the necessary fee.

normal diet, HFD: high lipid diet, Olt: oltipraz, **: p<0.01 compared to a ND group, and ##: p<0.01 compared to only HFD treated group)

Figure 5:
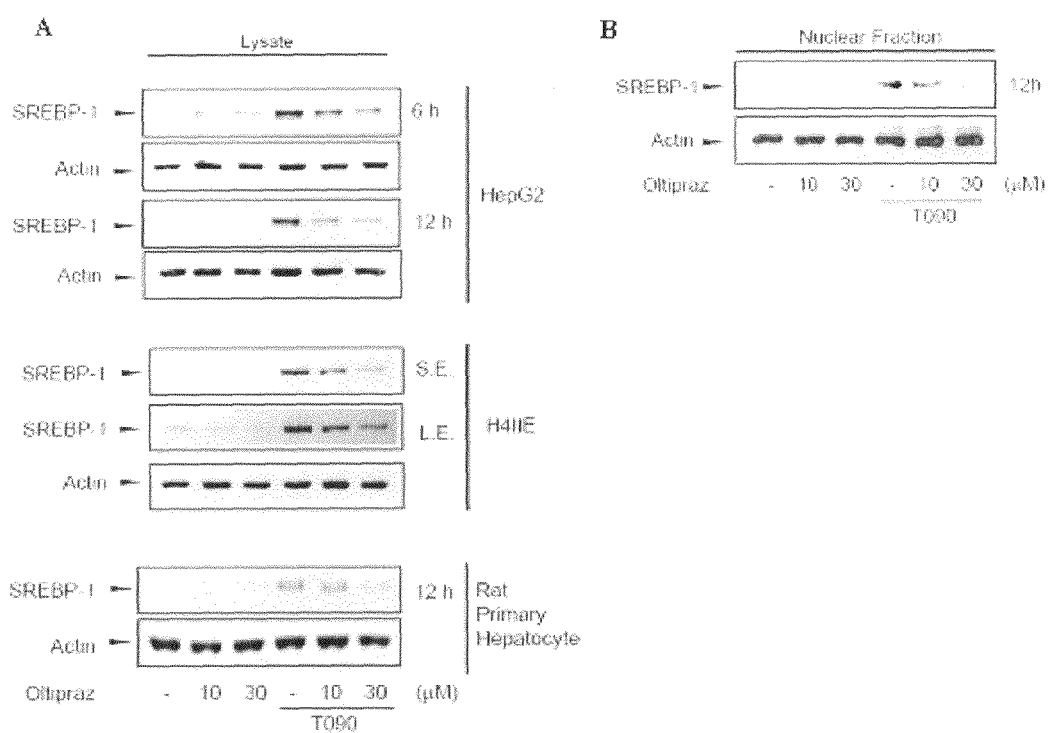

FIG. 5 shows results of oltipraz treatment on expression of a SREBP-1 protein after H4IIE and HepG2, which are liver cell lines, and rat primary cultured liver cells were treated with T0901317 that is a LXRα activator. SREBP-1 protein was identified by western blot assay. (S.E: short-time film exposure, L.E: long-time film exposure, A: whole cell extract lysate, and B: nuclear fraction of HepG2 cell)

Figure 6:
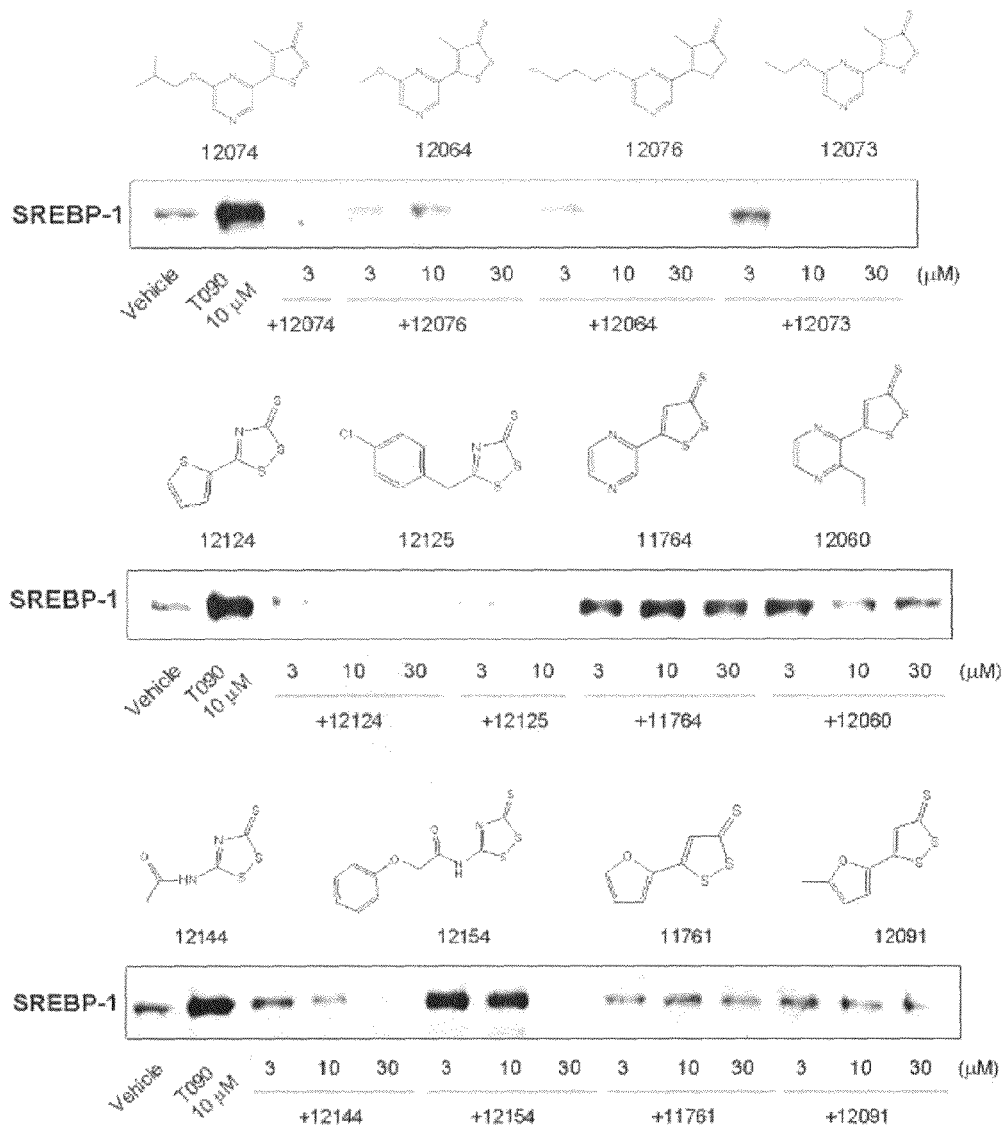
Figure 7:
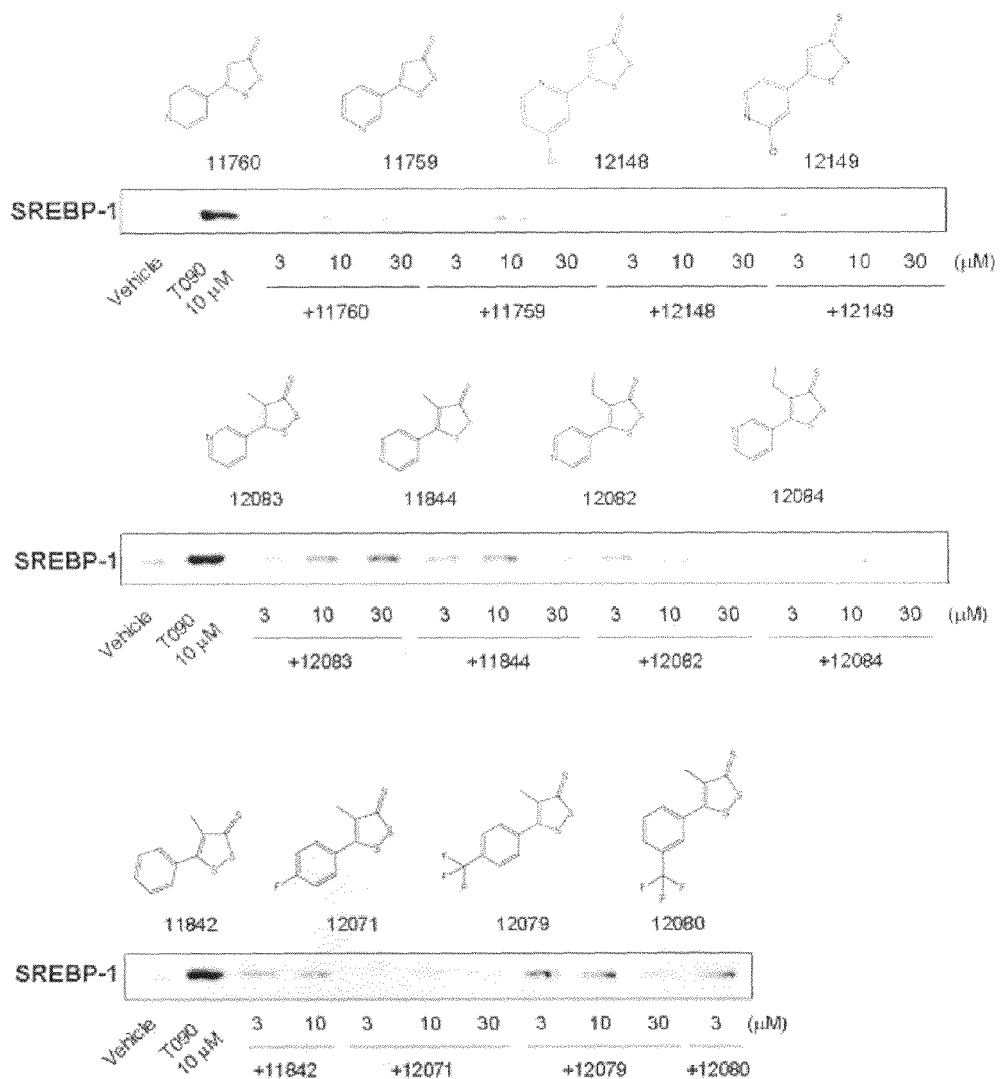
Figure 8:
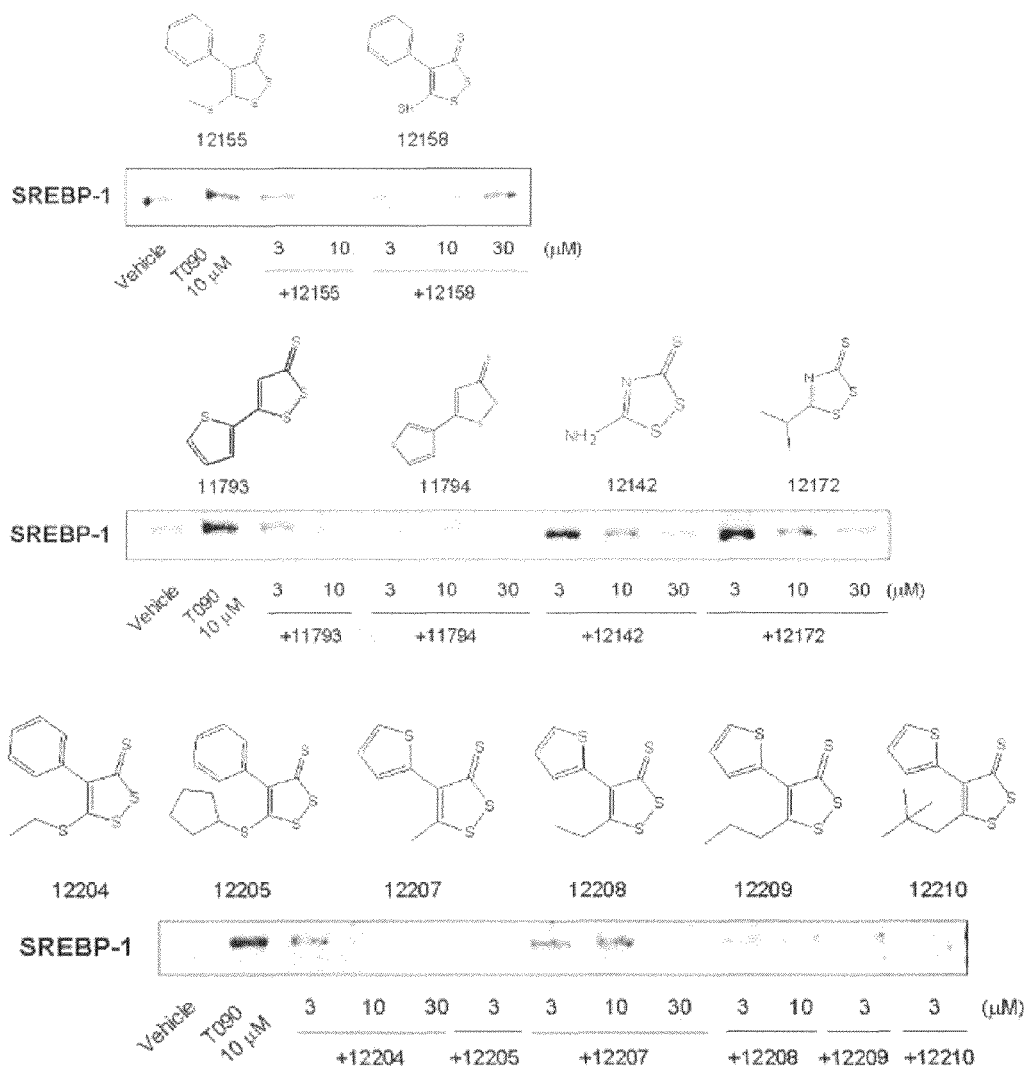

FIGS. 6 through 8 show western blot results of 1,2-dithiolthione derivatives with respect to SREBP-1 whose expression was increased due to treatment with a LXRα activator.

Figure 9:
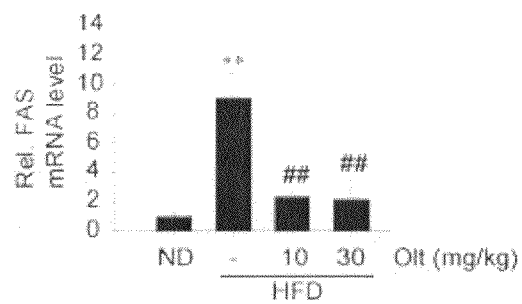
Figure 9:
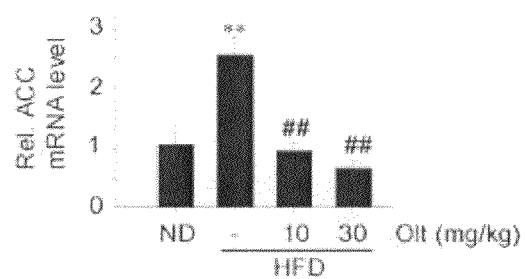

FIG. 9 shows comparative amounts of high lipid diet-derived lipogenic genes (FAS, is ACC) expressed in liver tissues when oltipraz was administered to a high lipid diet-derived fatty liver animal model.

Figure 10:
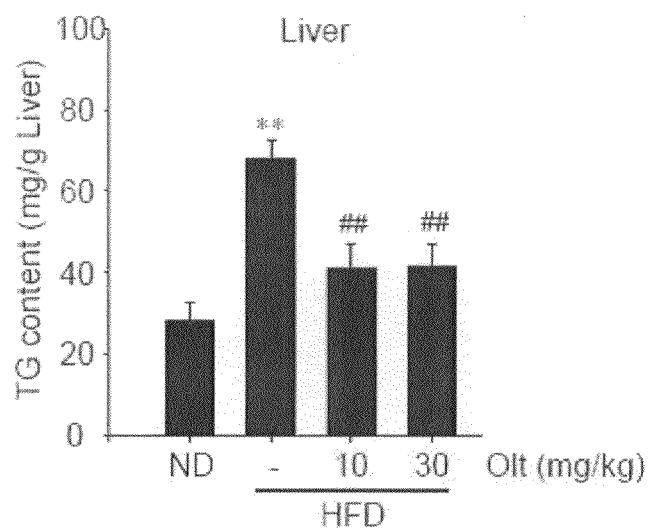

FIG. 10 shows results of oltipraz treatment on amounts of triglyceride in liver tissues in a high lipid diet-derived fatty liver animal model when olitpraz was administered to the high lipid diet-derived fatty liver animal model.

Figure 11:
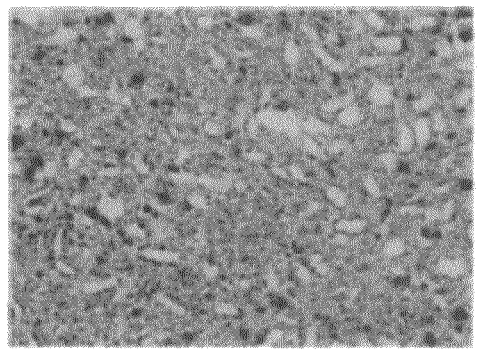
Figure 11:
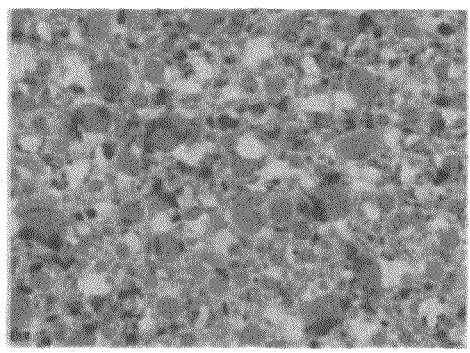
Figure 11:
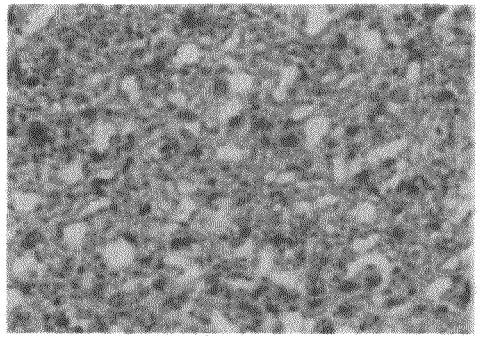
Figure 11:
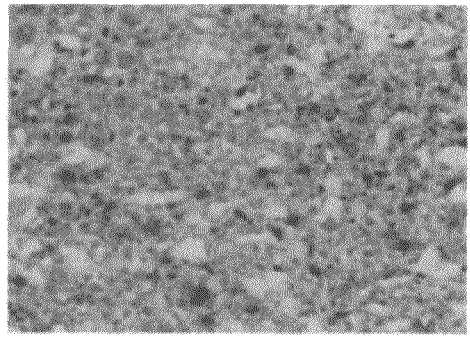

FIG. 11 shows images of liver tissues stained with Oil-Red-O when oltipraz was administered to a high lipid diet-derived fatty liver animal model.

MODE FOR INVENTION

Figure 2:
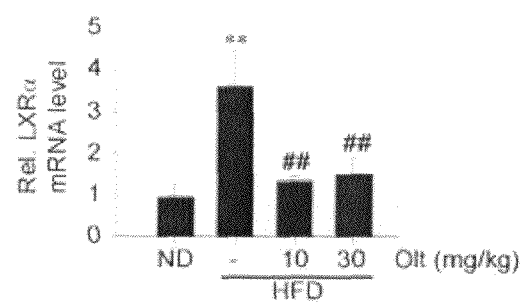
FIG. 2 shows results of oltipraz treatment on LXRα whose expression was increased due to a high lipid diet. The results are shown in values relative to LXRα mRNA of a normal diet group. (ND: normal diet, HFD: high lipid diet, Olt: oltipraz, **; $p<0.01$ compared to ND group, and ##: $p<0.01$ compared to only HFD treated group)
Figure 3:
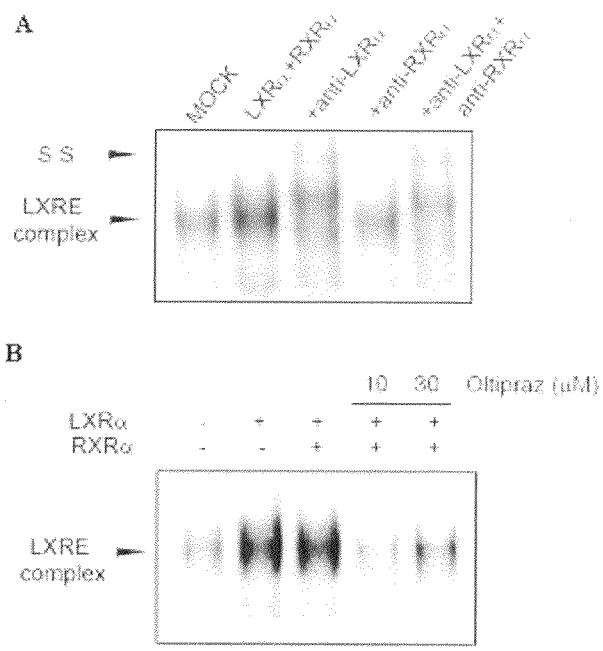
FIG. 3 shows oltipraz treatment effects on LXRα activity that was increased by overexpression of LXRα. (S.S: supershift)

The present invention is based on the fact that 1,2-dithiolthione derivatives such as oltipraz inhibit activity of LXRα and the expression and activity of sterol response element binding protein-1 (SREBP-1) that is a cellular protein for controlling expression of lipogenic genes. The inventors of the present invention found that expression of LXRα in a mouse which has an activity of LXRα increased due to high lipid diets is inhibited by oltipraz (FIG. 2), and that the binding capability of LXRα with respect to LXR-binding DNA element is also decreased by oltipraz (FIG. 3). Also, the inventors of the present invention found that expression of SREBP-1 that is increased when T0901317, which is known as a LXRα activator, is applied to a hepatocyte cell line is inhibited by oltipraz or other 1,2-dithiolthione derivatives (FIGS. 4 through 8).

When 1,2-dithiolthione derivatives such as oltipraz are administered, the expression and activity of SREBP-1 which is a key transcription factor that controls the gene expression of lipogenic enzymes by controlling activity of LXRα are inhibited, and furthermore triglyceride accumulation that occurs due to metabolism disorder-induced liver steatosis in liver tissue is prevented by inhibiting expression of the lipogenic genes. Thus, since the pharmaceutical composition according to the present invention contains 1,2-dithiolthione derivatives as an effective component, the pharmaceutical composition can be effective for preventing and treating liver steatosis. The inventors of the present invention found that when oltipraz is administered to liver tissue in which the amount of triglyceride is increased by administration of high lipid diet, the amount of triglyceride is significantly decreased (FIG. 10 and FIG. 11) and expression of fatty acid synthase (FAS) and acetyl CoA carboxylase (ACC), which are enzymes for synthesizing a fatty acid that is increased in the mouse administered with a high lipid diet, is also significantly inhibited (FIG. 9).

Based on the findings of the inventors of the present invention, the present invention provides a pharmaceutical composition for preventing and treating a disease caused by the overexpression or overactivity of LXRα or SREBP-1, wherein the pharmaceutical composition contains: as an effective component a 1,2-dithiolthione derivative represented by Formula 1 below, a pharmaceutically acceptable salt thereof, a solvate thereof, or a hydrate thereof or prodrug thereof; and a pharmaceutically acceptable carrier.

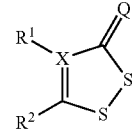

[Formula 1]

where X is carbon or nitrogen, Q is sulfur, oxygen, or —S═O, and $R^1$ and $R^2$ are each independently selected from the group consisting of a hydrogen atom, $C_{1-7}$-alkyl, $C_{3-7}$-cycloalkyl, $C_{1-7}$-alkoxy, $C_{3-7}$-cycloalkoxy, $C_{1-7}$-alkylthio, $C_{3-7}$-cycloalkylthio, $C_{1-7}$-alkynyl, $C_{1-7}$-alkylsulfonyl, $C_{1-7}$-alkylaminocarbonyl, HO—$C_{1-7}$-alkyl, HS—$C_{1-7}$-alkyl, hydroxy, thiol, halogen, carboxyl, nitro, cyano, $C_{1-7}$-alkylcarbonyl, $C_{1-7}$-alkoxycarbonyl, $C_{1-7}$-alkylcarbonyloxy, $C_{1-4}$-alkylcarbonyl-$C_{1-4}$-alkyl, $C_{1-4}$-alkoxy-$C_{1-4}$-alkyl, $C_{1-4}$-alkylthio-$C_{1-4}$-alkyl, amino, $C_{1-7}$-alkylamino, $C_{1-7}$-alkylcarbonylamino, $C_{1-4}$-alkoxy-$C_{1-4}$-alkylamino, $C_{1-4}$-alkylthio-$C_{1-4}$-alkylamino, $C_{1-4}$-alkylsulfoneamino, phenyl, heteroaryl, phenyl-$C_{1-4}$-alkyl, heteroaryl-$C_{1-4}$-alkyl, phenyl-$C_{1-4}$-alkoxy-$C_{1-4}$-alkyl, phenyl-$C_{1-4}$-alkylthio-$C_{1-4}$-alkyl, phenoxy-$C_{1-4}$-alkyl, phenylthio-$C_{1-4}$-alkyl, phenylcarbonylamino, phenoxy-$C_{1-4}$-alkylcarbonylamino, phenyl-$C_{1-4}$-alkoxy-$C_{1-4}$-alkylcarbonylamino, heteroaryloxy-$C_{1-4}$-alkyl, heteroarylthio-$C_{1-4}$-alkyl, and heteroaryl-$C_{1-4}$-alkylthio-$C_{1-4}$-alkyl, wherein the heteroaryl refers to a 5 or 6-membered cyclic compound that contains at least one hetero atom selected from the group consisting of nitrogen, sulfur, and oxygen; the phenyl and heteroaryl may be substituted or unsubstituted and an available substituent may be selected from the group consisting of halogen, $C_{1-7}$-alkyl, $C_{1-7}$-alkoxy, $C_{1-7}$-haloalkyl, $C_{1-7}$-alkylthio, $C_{1-7}$-alkenyloxy, $C_{1-4}$-alkylcarbonyl, $C_{1-4}$-alkylamino, nitro, amino, cyano, HO—$C_{1-4}$-alkyl, HS—$C_{1-4}$-alkyl, HO—$C_{1-7}$-alkoxy, HO—$C_{1-7}$-alkylthio, HS—$C_{1-7}$-alkylthio, HS—$C_{1-7}$-alkoxy, thiol, hydroxy, and carboxyl, and when substituted, the phenyl and heteroaryl may be mono-substituted or multi-substituted; the phenyl and heteroaryl may be each independently fused with at least one benzene or the heteroaryl described above; and the fused phenyl and heteroaryl may be substituted or unsubstituted and an available substituent may be selected from the group consisting of halogen, $C_{1-7}$-alkyl, $C_{1-7}$-alkoxy, $C_{1-7}$-haloalkyl, $C_{1-7}$-alkylthio, $C_{1-7}$-alkenyloxy, $C_{1-4}$-alkylcarbonyl, $C_{1-4}$-alkylamino, nitro, amino, cyano, HO—$C_{1-4}$-alkyl, HS—$C_{1-4}$-alkyl, HO—$C_{1-7}$-alkoxy, HO—$C_{1-7}$-alkylthio, HS—$C_{1-7}$-alkylthio, HS—$C_{1-7}$-alkoxy, thiol, hydroxy, and carboxyl, and when substituted, the phenyl and heteroaryl may be mono-substituted or multi-substituted.

The disease caused by the overexpression or overactivity of LXRα or SREBP-1 may be, but is not limited to, hypertension caused by renin, aldosteronism, adrenoleukodystrophy, glomerulosclerosis, proteinuria, nephropathy, liver steatosis, hypertriglyceridemia, or hyperreninemia. Thus, the present invention provides a pharmaceutical composition for preventing and treating hypertension caused by renin, aldosteronism, adrenoleukodystrophy, glomerulosclerosis, proteinuria, nephropathy liver steatosis, hypertriglyceridemia, or hyperreninemia, wherein the pharmaceutical composition contains a 1,2-dithiolthione derivative represented by Formula 1 as an effective component, and a pharmaceutically acceptable carrier.

The present invention also provides a method for inhibiting the expression or activity of LXRα or SREBP-1 in vitro or in vivo comprising administering a pharmaceutical composition, wherein the pharmaceutical composition contains: as an effective component a 1,2-dithiolthione derivative represented by Formula 1 below, a to pharmaceutically acceptable salt thereof, a prodrug thereof, a solvate thereof or a hydrate thereof; and a pharmaceutically acceptable carrier.

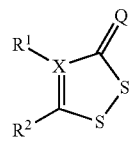

[Formula 1]

where X is carbon or nitrogen, Q is sulfur, oxygen, or —S=O, and $R^1$ and $R^2$ are each independently selected from the group consisting of a hydrogen atom, $C_{1-7}$-alkyl, $C_{3-7}$-cycloalkyl, $C_{1-7}$-haloalkyl, $C_{1-7}$-alkoxy, $C_{3-7}$-cycloalkoxy, $C_{1-7}$-alkylthio, $C_{3-7}$-cycloalkylthio, $C_{1-7}$-alkenyl, $C_{1-7}$-alkynyl, $C_{1-7}$-alkylsulfonyl, $C_{1-7}$-alkylaminocarbonyl, hydroxy, thiol, halogen, carboxyl, nitro, cyano, $C_{1-7}$-alkylcarbonyl, $C_{1-7}$-alkoxycarbonyl, $C_{1-7}$-alkylcarbonyloxy, $C_{1-4}$-alkylcarbonyl-$C_{1-4}$-alkyl, $C_{1-4}$-alkoxy-$C_{1-4}$-alkyl, $C_{1-4}$-alkylthio-$C_{1-4}$-alkyl, amino, $C_{1-7}$-alkylcarbonylamino, $C_{1-4}$-alkoxy-$C_{1-4}$-alkylamino, $C_{1-4}$-alkylthio-$C_{1-4}$-alkylamino, $C_{1-4}$-alkylsulfoneamino, phenyl, heteroaryl, phenyl-$C_{1-4}$-alkyl, heteroaryl-$C_{1-4}$-alkyl, phenyl-$C_{1-4}$-alkoxy-$C_{1-4}$-alkyl, phenyl-$C_{1-4}$-alkylthio-$C_{1-4}$-alkyl, phenoxy-$C_{1-4}$-alkyl, phenylthio-$C_{1-4}$-alkyl, phenylcarbonylamino, phenoxy-$C_{1-4}$-alkylcarbonylamino, phenyl-$C_{1-4}$-alkoxy-$C_{1-4}$-alkylcarbonylamino, heteroaryloxy-$C_{1-4}$-alkyl, heteroarylthio-$C_{1-4}$-alkyl, and heteroaryl-$C_{1-4}$-alkylthio-$C_{1-4}$-alkyl, wherein the heteroaryl refers to a 5 or 6-membered cyclic compound that contains at least one hetero atom selected from the group consisting of nitrogen, sulfur, and oxygen; the phenyl and heteroaryl may be substituted or unsubstituted and an available substituent may be selected from the group consisting of halogen, $C_{1-7}$-alkyl, $C_{1-7}$-alkoxy, $C_{1-7}$-haloalkyl, $C_{1-7}$-alkylthio, $C_{1-7}$-alkenyloxy, $C_{1-4}$-alkylcarbonyl, $C_{1-4}$-alkylamino, nitro, amino, cyano, HO—$C_{1-4}$-alkyl, HS—$C_{1-4}$-alkyl, HO—$C_{1-7}$-alkoxy, HO—$C_{1-7}$-alkylthio, HS—$C_{1-7}$-alkylthio, HS—$C_{1-7}$-alkoxy, thiol, hydroxy, and carboxyl, and when substituted, the phenyl and heteroaryl may be mono-substituted or multi-substituted; the phenyl and heteroaryl may be each independently fused with at least one benzene or the heteroaryl described above; and the fused phenyl and heteroaryl may be substituted or unsubstituted and an available substituent may be selected from the group consisting of halogen, $C_{1-7}$-alkyl, $C_{1-7}$-alkoxy, $C_{1-7}$-haloalkyl, $C_{1-7}$-alkylthio, $C_{1-7}$-alkenyloxy, $C_{1-4}$-alkylcarbonyl, $C_{1-4}$-alkylamino, nitro, amino, cyano, HS—$C_{1-4}$-alkyl, HO—$C_{1-7}$-alkoxy, HO—$C_{1-7}$-alkylthio, HS—$C_{1-7}$-alkylthio, HS—$C_{1-7}$-alkoxy, thiol, hydroxy, and carboxyl, and when substituted, the phenyl and heteroaryl may be mono-substituted or multi-substituted.

The present invention also provides a method for preventing or treating a disease or condition associated with the over-expression or over-activity of LXRα or SREBP-1 comprising administering a pharmaceutical composition, wherein the pharmaceutical composition contains: as an effective component a 1,2-dithiolthione derivative represented by Formula 1 below, a pharmaceutically acceptable salt thereof, a prodrug thereof, a solvate thereof or a hydrate thereof; and a pharmaceutically acceptable carrier.

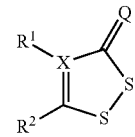

[Formula 1]

where X is carbon or nitrogen, Q is sulfur, oxygen, or —S=O, and $R^1$ and $R^2$ are each independently selected from the group consisting of a hydrogen atom, $C_{1-7}$-alkyl, $C_{3-7}$-cycloalkyl, $C_{1-7}$-haloalkyl, $C_{1-7}$-alkoxy, $C_{3-7}$-cycloalkoxy, $C_{1-7}$-alkylthio, $C_{3-7}$-cycloalkylthio, $C_{1-7}$-alkenyl, $C_{1-7}$-alkynyl, $C_{1-7}$-alkylsulfonyl, $C_{1-7}$-alkylaminocarbonyl, HO—$C_{1-7}$-alkyl, HS—$C_{1-7}$-alkyl, hydroxy, thiol, halogen, carboxyl, nitro, cyano, $C_{1-7}$-alkylcarbonyl, $C_{1-7}$-alkoxycarbonyl, $C_{1-7}$-alkylcarbonyloxy, $C_{1-4}$-alkylcarbonyl-$C_{1-4}$-alkyl, $C_{1-4}$-alkoxy-$C_{1-4}$-alkyl, $C_{1-4}$-alkylthio-$C_{1-4}$-alkyl, amino, $C_{1-7}$-alkylamino, $C_{1-7}$-alkylcarbonylamino, $C_{1-4}$-alkoxy-$C_{1-4}$-alkylamino, $C_{1-4}$-alkylthio-$C_{1-4}$-alkylamino, $C_{1-4}$-alkylsulfoneamino, phenyl, heteroaryl, phenyl-$C_{1-4}$-alkyl, heteroaryl-$C_{1-4}$-alkyl, phenyl-$C_{1-4}$-alkoxy-$C_{1-4}$-alkyl, phenyl-$C_{1-4}$-alkylthio-$C_{1-4}$-alkyl, phenoxy-$C_{1-4}$-alkyl, phenylthio-$C_{1-4}$-alkyl, phenylcarbonylamino, phenoxy-$C_{1-4}$-alkylcarbonylamino, phenyl-$C_{1-4}$-alkoxy-$C_{1-4}$-alkylcarbonylamino, heteroaryloxy-$C_{1-4}$-alkyl, heteroarylthio-$C_{1-4}$-alkyl, and heteroaryl-$C_{1-4}$-alkylthio-$C_{1-4}$-alkyl, wherein the heteroaryl refers to a 5 or 6-membered cyclic compound that contains at least one hetero atom selected from the group consisting of nitrogen, sulfur, and oxygen; the phenyl and heteroaryl may be substituted or unsubstituted and an available substituent may be selected from the group consisting of halogen, $C_{1-7}$-alkyl, $C_{1-7}$-alkoxy, $C_{1-7}$-haloalkyl, $C_{1-7}$-alkylthio, $C_{1-7}$-alkenyloxy, $C_{1-4}$-alkylcarbonyl, $C_{1-4}$-alkylamino, nitro, amino, cyano, HO—$C_{1-4}$-alkyl, HS—$C_{1-4}$-alkyl, HO—$C_{1-7}$-alkoxy, HO—$C_{1-7}$-alkylthio, HS—$C_{1-7}$-alkylthio, HS—$C_{1-7}$-alkoxy, thiol, hydroxy, and carboxyl, and when substituted, the phenyl and heteroaryl may be mono-substituted or multi-substituted; the phenyl and heteraryl may be each independently fused with at least one benzene or the heteroaryl described above; and the fused phenyl and heteroaryl may be substituted or unsubstituted and an available substituent may be selected from the group consisting of halogen, $C_{1-7}$-alkyl, $C_{1-7}$-alkoxy, $C_{1-7}$-haloalkyl, $C_{1-7}$-alkylthio, $C_{1-7}$-alkenyloxy, $C_{1-4}$-alkylcarbonyl, $C_{1-4}$-alkylamino, nitro, amino, cyano, HO—$C_{1-4}$-alkyl, HO—$C_{1-7}$-alkoxy, HO—$C_{1-7}$-alkylthio, HS—$C_{1-7}$-alkylthio, HS—$C_{1-7}$-alkoxy, thiol, hydroxy, and carboxyl, and when substituted, the phenyl and heteroaryl may be mono-substituted or multi-substituted.

In some embodiments of methods of treating or preventing a disease or condition mediated by an LXRα or SREBP-1, the disease or a condition is for example, liver steatosis, hypertriglyceridemia, hyperreninemia, hypertension caused by renin, aldosteronism, adrenoleukodystrophy, glomerulosclerosis, proteinuria, or nephropathy. In some embodiments, the compounds disclosed herein are used to ameliorate and/or slow the progression of one or more of these disease or conditions. The 1,2-dithiolthione derivative contained in the pharmaceutical composition according to the present invention may include an organic compound that includes 1,2- dithiol-3-thione and a bicyclic molecule and a derivative organic compound of the organic compound. The bicyclic molecule may be pyrazine, pyridazine, pyrimidine, thiazole, or thiophene (Table 1).

TABLE 1

Example of compounds containing 1,2-dithiol-3-thione for inhibiting the expression of SREBP-1

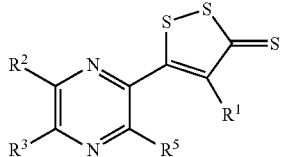

R$^1$: —H, -Alkyl(C$_{1-x}$)
R$^2$: —H, -Halogen, -Alkoxy
R$^3$: —H, -Alkyl(C$_{1-x}$)
R$^4$: —O
R$^5$: —H, -Alkyl(C$_{1-x}$)
(one among R$^2$ to R$^5$ is substituted)

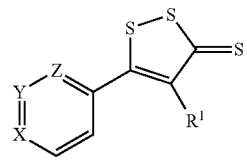

R$^1$: —H, -Alkyl(C$_{1-x}$)
one among X, Y and Z is
—N and others are C

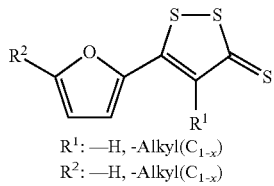

R$^1$: —H, -Alkyl(C$_{1-x}$)
R$^2$: —H, -Alkyl(C$_{1-x}$)

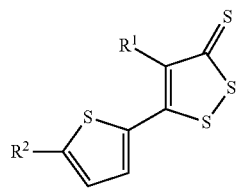

R$^1$: —H, -Alkyl(C$_{1-x}$)
R$^2$: —H, -Alkyl(C$_{1-x}$)
-Halogen,

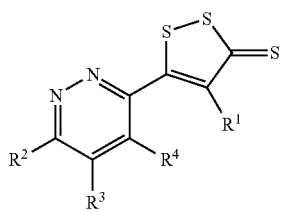

R$^1$: —H, -Alkyl(C$_{1-x}$)
R$^2$: —H, -Alkyl(C$_{1-x}$)
R$^3$: —H, -Alkyl(C$_{1-x}$)
R$^4$: —H, -Alkyl(C$_{1-x}$)

TABLE 1-continued

Example of compounds containing 1,2-dithiol-3-thione for inhibiting the expression of SREBP-1

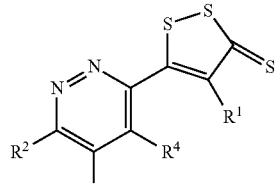

R$^1$: —H, -Alkyl(C$_{1-x}$)
R$^2$: —H, -Alkyl(C$_{1-x}$)
R$^3$: —H, -Alkyl(C$_{1-x}$)
R$^4$: —H, -Alkyl(C$_{1-x}$)

The pharmaceutical composition according to the present invention may include pharmaceutically acceptable salts that are formed using the compounds described above, a solvate thereof, a hydrate thereof or a prodrug thereof. A pharmaceutically acceptable addition salt may be a pharmaceutically acceptable acid addition salt or a pharmaceutically acceptable base addition salt. The term 'pharmaceutically acceptable acid addition salt' used in the present specification may include a non-toxic acid addition salt that is formed using the compound represented by Formula 1 and is therapeutically active. The compound represented by Formula 1 originally has a basic characteristic and when treated with a suitable acid, the compound represented by Formula 1 may be converted into a pharmaceutically acceptable acid addition salt of the compound represented by Formula 1. The suitable acid may be an inorganic acid or an organic acid. Examples of the inorganic acid of the suitable acid include a halogenated hydrogen acid such as a hydrochloric acid or a bromic acid; a sulfuric acid; a nitric acid; and a phosphoric acid. Examples of the organic acid of the suitable acid include an acetic acid, a trifluoroacetic acid, a propanic acid, a hydroxyacetic acid, a lactic acid, a pyruvic acid, oxalic acid, malonic acid, a succinic acid (that is, butanedioic acid), a maleic acid, a fumaric acid, malic acid, a tartaric acid, a citric acid, a methanesulfonic acid, an ethanesulfonic acid, a benzene sulfonic acid, p-toluenesulfonic acid, a cyclamic acid, a salicylic acid, p-amino-salicylic acid, and a pamoic acid. The converted compound having an acidic characteristic may also be converted into a pharmaceutically acceptable base addition salt thereof when treated with a suitable organic or inorganic base. A suitable base addition salt may be, for example, an ammonium salt; alkali and alkali earth-based salts such as a lithium salt, a sodium salt, a potassium salt, a magnesium salt, or a calcium salt; a salt with an organic base such as a benzathine salt, an N-methyl-D-glucamine salt, or a hydrabamie salt; or a salt with an amino acid such as arginine or lysine.

The pharmaceutical composition according to the present invention may be formulated into a unit administration type preparation that is suitable for oral administration or an injectable preparation using a conventional method in the pharmaceutical art and then administered. The unit administration type preparation that is suitable for oral administration may be a hard or soft capsule, a tablet, a powder, a suspension, or syrup. The unit administration type preparation that is suitable for oral administration may include, in addition to at least one pharmaceutically active component, at least one pharmaceutically ineffective inactive conventional carrier. The at least one pharmaceutically ineffective inactive conventional carrier may include, for example, an excipient, a binder, a disintegrant, and a lubricant. Examples of an excipient include powder, lactose, carboxymethylcellulose, and kaolin. Examples of a binder include water, gelatin, alcohol, glucose, Arabia rubber, and tragacanth rubber. Examples of a disintegrant include powder, dextrine, and sodium alginate. Examples of a lubricant include talc, staric acid, magnesium stearate, and fluid paraffin. The pharmaceutical composition according to the present invention may further include a dissolution assistant for dissolving.

A daily dose of the pharmaceutical composition according to the present invention may vary according to the seriousness of a disease, the development time of the disease, and the age, health state, and a complication of a patient. For example, the pharmaceutical composition according to the present invention may be administered at a dose of 1 to 500 mg, specifically 30 to 200 mg to an adult, in one day. The dose may be administered as a bolus or divided into several portions.

The present invention will be described in further detail with reference to the following experimental examples. These experimental examples are for illustrative purposes only and are not intended to limit the scope of the present invention.

Reference Example 1

Test Animal and Diet

Figure 1:
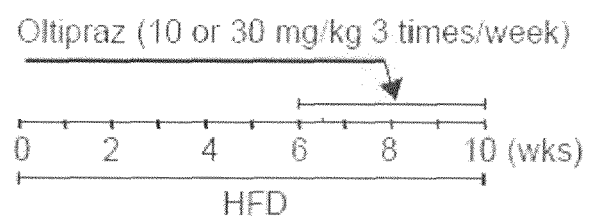
FIG. 1 shows an oltipraz administration schedule.

Male C57BL/6 mice (average weight of 25 to 30 g) as test animals were purchased from Charles River Orient (Seoul, Korea). For at least one week before being tested, the mice were acclimatized to the surrounding environment in the animal test research center of the College of Pharmacy, Seoul National University, that is, humidity of 55±5%, temperature of 22±2° C., and controlled ventilation. The mice were repeatedly and alternately exposed to light and then placed in the dark for a time interval of 12 hours (from 7 A.M. to 7 P.M). During the test, the amounts of food and water the mice consumed were not significantly changed. The weight and state of the mice were measured once a week. Two groups of mice were respectively raised with a high lipid diet (Dyets Inc., Bethlehem) and a normal diet for 10 weeks. For the last four weeks in each case, oltipraz (10 or 30 mg/kg, 3 times/week) was administered to the mice (FIG. 1). Each group consisted of a total of 10 mice.

Reference Example 2

Sample Preparation

Oltipraz and 1,2-dithiolthione derivative were provided by CJ Co., Ltd. A 1,2-dithiolthione derivative used in the present invention can be manufactured using a method disclosed in KR No. 10-0604261. A high lipid diet for inducing a fatty liver was purchased from Dyet Co., a USA company. The oltipraz was diluted with 40% PEG200 to obtain a target concentration.

Reference Example 3

Real Time-RT PCR

Total RNA (2 μg) and $d(T)_{16}$ primer which were extracted from the liver of mice, and an AMV reverse transcriptase were used to obtain cDNA. The relative amounts of genes were quantified by realtime RT-PCR using a CyBr green dye. The realtime RT-PCR was Light-cycler$^{2.0}$ produced by Roche (Mannheim, Germany). A PCR was performed using the method of the manufacturer and Light-cycler software 4.0 program was used to analyze the relative amount of the respective genes.

Reference Example 4

Western Blot

Sodium dodecylsulfate-polyacrylamide gel electrophoresis (SDS-PAGE) was performed using a Mighty Small II SE 250 apparatus according to a Laemmli UK method (1970). A dissolution aliquot of a liver sample was diluted with a sample dilution buffer solution [63 mM Tris (pH.6.8), 10% glycerol, 2% SDS, 0.0013% bromophenol blue, 5% β-mercaptoethanol] and then, electrophoresis was performed using 7.5% and 9% gel in an electrode buffer solution (15 g of Tris, 72 g of glycine, and 5 g of SDS were contained per 1 L of solution). After the electrophoresis was performed, proteins of the gel were transferred to a nitrocellulose sheet in a buffer solution [25 mM Tris, 192 mM glycine, 20% v/v methanol (pH.8.3)] in an electrophoresis system at 190 mAmps for one hour. Anti-SREBP-1 was reacted as a primary antibody and then, horseradish peroxidase-conjugated goat anti-rabbit IgG was reacted as a secondary antibody for one hour. Then, an ECL chemiluminescence system (Amersham, Gaithesberg, Mass.) was used to visualize the immunoreactive protein. Equal loading of the protein amount in the respective samples was identified using an anti-β-actin antibody (Sigma, St. Louis, Mo.).

Reference Example 5

Assay Method

Data that will be shown in the following experimental examples was obtained by using a pharmaceutical calculation program. That is, significance between various experimental groups was examined by mono-direction quadratic variance assay (Fisher, R. A., *Statistical Methods for Research Workers, Edinburgh: Oliver & Boyd,* 1925) and then, the results were determined by Newman Keuls methods (Norman G R et al., Biostatistics: The Bare Essentials, 2000) ($*p<0.05$, $**p<0.01$).

Experimental Example 1

Oltipraz Treatment Effect on Increased Lxrα Expression

Mice were raised with a high lipid diet and a normal diet for 10 weeks. The expression of LXRα in liver tissue of a group of mice raised with the high lipid diet and administered with oltipraz (10-30 mg/kg, 3 times/week) that is a 1,2-dithiolthione compound for the last four weeks was evaluated. mRNA was isolated from the liver tissue, cDNA was synthesized by RT-PCR, and then real-time PCR was performed thereon using a particular primer (mouse LXR, 5'-TGCCATCAG-CATCTTCTCTG-3' (sense) and 5'-GGCTCACCAGCT-TCATTAGC-3' (antisense)). The expression level of LXRα mRNA of a normal diet group (ND) was set to 1 and the relative expression levels of a high lipid diet group or a high lipid diet and oltipraz-administered group were measured. The results are shown in FIG. 2. Thus, it can been seen that expression of LXRα, which is a intracellular lipid sensor, is significantly increased due to a high lipid diet ($p<0.01$) and an increase in LXRα expression is inhibited by administrating oltipraz ($p<0.01$).

Experimental Example 2

Inhibition Effects of Oltipraz Treatment on Activity of LXRα

LXRα controls expression of a gene by forming a dimer together with RXRα and binding to a particular region (LXRE) existing in a target gene promoter. Whether a binding capability of LXRE is changed by oltipraz treatment was identified by gel-shift assay. LXRE double-stranded oligonucleotide of a SREBP-1c gene was labeled with a radio active isotope at 5'-terminal by using [γ-$^{32}$P]ATP and T4 polynucleotide kinase, and then the labeled probe (1 ml, >10$^6$ cpm) was reacted with nuclear fraction proteins in a binding buffer solution. The reaction solution was subjected to electrophoresis in 4% polyacrylamide gel and then assayed by autoradiography. A LXRE oligonucleotide sequence used in test was 5'-CAGTGACCGCCAGTAACCCCAGC-3'. DNA binding specificity was identified by cold probe titration and supershift assay. For the cold probe titration, 20 times greater (molar base) un-labeled oligonucleotides were reacted in advance. For supershift assay, antibody against LXRα or RXRα (2 μg) was reacted with a reaction mixture at room temperature for about 30 minutes, and then the probe labeled with a radio active isotope was added thereto and further reacted for 30 minutes and then subjected to electrophoresis.

When LXRα and RXRα were overexpressed, the intensity of the slow migrating bands was increased, compared to a mock (see first and second bands in FIG. 3A). When the supershift assay was performed using antibodies against LXRα and RXRα, DNA protein binding was reduced due to antibodies against LXRα and RXRα and super-shifted bands were formed (see third to fifth bands FIG. 3A). Such results support DNA binding specificity of LXRα/RXRα complex.

When oltipraz was administered, the increase in the intensity of the retarded bands (see first through third bands in FIG. 3) was reduced (see fourth and fifth bands of is FIG. 3B). Such results show that a binding capability of LXRα with respect to DNA was substantially decreased due to treatment with oltipraz.

Experimental Example 3

Oltipraz Treatment Effect on SREBP-1 with Increased Expression

Figure 4:
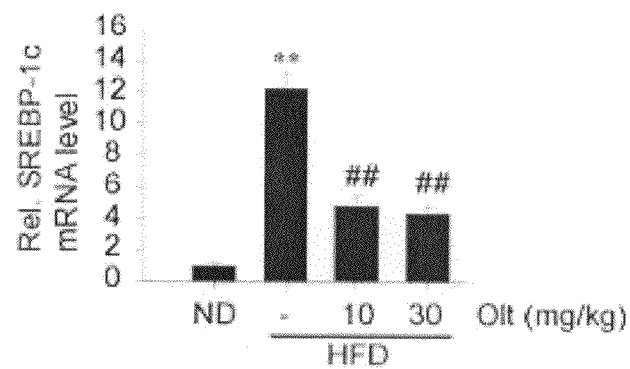
FIG. 4 shows results of oltipraz treatment on SREBP-1 whose expression was increased due to a high lipid diet. (ND.

Expression levels of SREBP-1 in liver tissues of the mice used in Experimental Example 1 were evaluated. mRNA was isolated from the liver tissues, cDNA was synthesized by RT-PCR, and then real-time PCR was performed thereon using a particular primer (mouse SREBP-1, 5'-AACGT-CACTTCCAGCTAGAC-3' (sense) and 5'-CCACTAAGGT-GCCTACAGAGC-3' (antisense)). The expression level of SREBP-1 mRNA of a normal diet group (ND) was set to 1 and the relative expression levels of a high lipid diet group or a high lipid diet and oltipraz-administered group were measured. The results are shown in FIG. 4. Thus, it can be seen that expression of SREBP-1 is significantly increased due to a high lipid diet (p<0.01) and an increase in SREBP-1 expression is inhibited by administrating oltipraz (p<0.01).

Experimental Example 4

Oltipraz Inhibition Effect on Expression and Activity of SREBP-1

H4IIE and HepG2 which are liver cell lines, and rat primary cultured liver cells were treated with 10901317 as a LXRα activator and then, a SREBP-1 protein was identified by western blot assay. The expression of SREBP-1 was remarkably increased within 12 hours after treatment with 10901317 (see fourth columns of respective gel images (shown in FIG. 5A). The increased expression of SREBP-1 protein was concentration-dependently reduced when treated with oltipraz (fifth and sixth columns of the respective gel images of FIG. 5A), which shows the expression of SREBP-1 is inhibited by oltipraz.

In addition, the increased nuclear localization of SREBP-1 in HepG2 cells treated with T0901317 was concentration-dependently reduced by treatment of oltipraz (FIG. 5B), which shows the activity of SREBP-1 is inhibited by oltipraz.

Cell fractions were isolated in the following manner. A low osmotic pressure is buffer solution [10 mM HEPES (pH 7.9), 10 mM KCl, 0.1 mM EDTA, 0.5% Nonidet P-40, 1 mM DTT and 0.5 mM phenylmethylsulfonylfluoride(PMSF)] was added to a liver cell line and then placed in ice for 10 minutes. Then, the resultant solution was centrifuged at 7200 g for five minutes and a supernatant was used as a cytoplasmic fraction. Separately, a high osmotic pressure buffer solution [20 mM HEPES (pH 7.9), 400 mM NaCl, 1 mM EDTA, 10 mM DTT, and 1 mM PMSF] was added to a liver cell line and then placed in ice for one hour. Then, the resultant solution was centrifuged at 15000 g for ten minutes and a supernatant used as a nuclear fraction. Separately, a solution buffer [10 mM HEPES (pH 7.9), 100 mM NaCl, 1 mM EDTA, 10% glycerol, 0.5% Triton X-100, 0.5% Nonidet P-40, 1 mM DTT and 0.5 mM PMSF] was added to a cell that had been washed with PBS and then lyzed in ice for one hour. Then, the resultant solution was centrifuged at 10,000 g for 10 minutes and a supernatant was used as a whole cell extract. These cell fractions were placed at a temperature of −70° C. before use. The concentration of protein was quantified by Bradford assay (Bio-Rad protein assay kit, Hercules, Calif., USA).

Experimental Example 5

1,2-Dithiolthione Derivatives Inhibition Effect on Expression of SREBP-1

Effects of 1,2-dithiolthione derivatives on LXRα activator (T0901317)-induced increased expression of SREBP-1 were evaluated using a H4IIE cell line. The expression of SREBP-1 that was increased when a H4IIE cell line was treated with T0901317 was inhibited by treatment with 1,2-dithiolthione derivatives (FIGS. 6 through 8).

Experimental Example 6

Oltipraz Inhibition Effect on Expression of FAS and ACC that are Fatty Acid Synthesis Enzymes Expression levels of FAS and ACC which are target genes of SREBP-1 in liver tissues of the mice used in Experimental Example 1 were evaluated. mRNA was isolated from the liver tissues and then cDNA was synthesized by RT-PCR, and then real-time PCR was performed thereon using a particular primer (mouse ACC1, 5'-GTCAGCGGATGGGCGGAATG-3' (sense) and 5'-CGCCGGATGCCATGCTCAAC-3' (antisense); mouse FAS, 5'-AGCGGCCATTTCCATTGCCC-3' (sense) and 5'-CCATGCCCAGAGGGTGGTTG-3' (antisense)). The expression level of FAS and ACC mRNA of a normal diet group (ND) was set to 1 and the relative expression levels of FAS or ACC mRNA of a high lipid diet group or a high lipid diet and oltipraz-administered group were measured. The results are shown in FIG. 9. Thus, it can be seen that expression of FAS and ACC is significantly increased due to a high lipid diet (p<0.01) and an increase in FAS and ACC expression is inhibited by administrating oltipraz (p<0.01).

Experimental Example 7

Oltipraz Inhibition Effect on Amount of Triglyceride Accumulated Due to High Lipid Diet in Live Tissue Effects of oltipraz on the amount of triglyceride in Experimental Example 1 in liver tissues of the mice used in Experimental Example 1 were evaluated. The amount of triglyceride in liver tissues is an index of fatty liver. After oltipraz was administered (Bae et al., Hepatology, 2007, 46: 730-739), the amount of triglyceride in liver tissues was measured. In regard to mice treated with a high lipid diet for 10 weeks, the amount of triglyceride in liver tissues was remarkably increased compared to a normal diet group (p<0.01), but when administered with oltipraz, the amount of triglyceride in liver tissues was significantly reduced (p<0.01) (FIG. 10).

Experimental Example 8

Oltipraz Therapeutic Effect on Liver Tissue of Animal Model Having Liver Steatosis Caused by High Lipid Diet Oltipraz therapeutic effects on the fatty liver caused by a high lipid diet used in Experimental Example 7 were identified by Oil-Red-O dying using a fat specific dye. Liver tissues of the fatty liver were fixed with 10% neutral formalin solution and subjected to conventional fixing procedures and dehydrating processes, and then the resultant liver tissues were embedded with paraffin. The embedded tissues were cut to a thickness of 4 µm and dyed with Oil-Red-O and then identified using an optical microscope. In regard to a high lipid diet group (HFD+vehicle), a red part dyed remarkably appeared; and in regard to an oltipraz-administered group (HFD+Oltipraz), the red part dyed was remarkably reduced (FIG. 11). Thus, it can be seen that Oltipraz therapeutic effects are high.

Various formulations containing 1,2-dithiolthione derivatives as an effective component were prepared.

Preparation Example 1

| | |
|---|---|
| Oltipraz | 25 mg |
| Lactose | 50 mg |
| Starch | 10 mg |
| Magnesium stearic acid | Appropriate |

These components were mixed and then a conventional tablet formulation method was performed thereon, thereby obtaining a tablet preparation.

Preparation Example 2

| | |
|---|---|
| 3-methyl-1,2-dithiol-3-thione | 50 mg |
| Lactose | 50 mg |
| Starch | 10 mg |
| Magnesium stearic acid | Appropriate |

These components were mixed and then a conventional tablet formulation method was performed thereon, thereby obtaining a tablet preparation.

Preparation Example 3

| | |
|---|---|
| 5-(6-methoxypyrazinyl)-4-methyl-1,2-dithiol-3-thione | 100 mg |
| Lactose | 50 mg |
| Starch | 10 mg |
| Magnesium stearic acid | Appropriate |

These components were mixed and then a conventional powder formulation method was performed thereon, thereby obtaining a powder preparation.

Preparation Example 4

| | |
|---|---|
| Oltipraz | 250 mg |
| Lactose | 50 mg |
| Starch | 10 mg |
| Magnesium stearic acid | Appropriate |

These components were mixed and then a conventional powder formulation method was performed thereon, thereby obtaining a powder preparation.

Preparation Example 5

| | |
|---|---|
| Oltipraz | 25 mg |
| Lactose | 30 mg |
| Starch | 28 mg |
| Talc | 2 mg |
| Magnesium stearic acid | Appropriate |

These components were mixed and then a gelatin soft capsule was filled therewith according to a conventional capsule formulation method in order to prepare a capsule preparation.

Preparation Example 6

| | |
|---|---|
| 5-(6-methoxypyrazinyl)-4-methyl-1,2-dithiol-3-thione | 50 mg |
| Lactose | 30 mg |
| Starch | 28 mg |
| Talc | 2 mg |
| Magnesium stearic acid | Appropriate |

These components were mixed and then a gelatin soft capsule was filled therewith according to a conventional capsule formulation method in order to prepare a capsule preparation.

Preparation Example 7

| | |
|---|---|
| Oltipraz | 100 mg |
| Isomerized sugar | 10 g |
| Sugar | 30 mg |
| Sodium CMC | 100 mg |
| Lemon flavor | Appropriate |

| | |
|---|---|
| Purified water | the balance (The entire amount of all the components was 100 ml) |

A suspension was prepared using these components according to a conventional suspension preparation method, and then a 100 ml brown bottle was filled therewith and sterilized, thereby obtaining a suspension preparation.

Preparation Example 8

| | |
|---|---|
| 3-methyl-1,2-dithiol-3-thione | 250 mg |
| Lactose | 30 mg |
| Starch | 20 mg |
| Magnesium stearic acid | Appropriate |

These components were homogeneously mixed and a polyethylene-coated pouch was filled therewith and then sealed, thereby preparing a powder preparation.

Preparation Example 9

One soft capsule contained:

| | |
|---|---|
| Oltipraz | 100 mg |
| Polyethyleneglycol 400 | 400 mg |
| Concentrate Glycerin | 55 mg |
| Purified Water | 35 mg |

Polyethyleneglycol and concentrate glycerin were mixed and then purified water was added thereto. While the temperature of the resultant mixture was maintained at about 60° C., a 1,2-dithiolthione derivative was added to the resultant mixture and then uniformly mixed by stirring at a rate of about 1,500 rpm. Then, while slowly mixing, the temperature was cooled to room temperature and then bubbles were removed using a vacuum pump, thereby preparing the content of a soft capsule. A surface film of the soft capsule was formed by soft treatment with a conventionally known gelatin or plasticizer. One capsule was prepared using 132 mg of gelatin, 52 mg of concentrate glycerin, 6 mg of 70% disorbitol solution, ethyl vanilline as a fragrance addition agent, and Carnauba wax as a coating agent, according to a conventional capsule formulation method.

INDUSTRIAL APPLICABILITY

The pharmaceutical composition according to the present invention is effective for preventing and treating a disease caused by the overexpression or overactivity of LXRα, or a disease caused by the overexpression or overactivity of SREBP-1. When the pharmaceutical composition is administered, the expression and activity of SREBP-1 are inhibited, wherein SREBP-1 is a key transcription factor that controls gene expression of lipogenic enzymes by adjusting activity of LXRα, and furthermore the expression of lipogenic genes is inhibited and thus, triglyceride accumulation in liver tissue, which occurs due to liver steatosis caused by metabolism disorder, is inhibited. Accordingly, pharmaceutical compositions containing the 1,2-dithiolthione derivatives as an effective component, according to the present invention, are effective for preventing and treating liver steatosis. Also, the pharmaceutical compositions are effective for preventing and treating hypertriglyceridemia, hyperreninemia, hypertension due to renin, aldosteronism, adrenoleukodystrophy, glomerulosclerosis, proteinuria, and nephropathy.

The invention claimed is:

1. A method for treating liver steatosis, comprising administering an effective amount of a compound selected from the group consisting of the following compounds, or a pharmaceutically acceptable salt thereof, to a subject in need thereof:

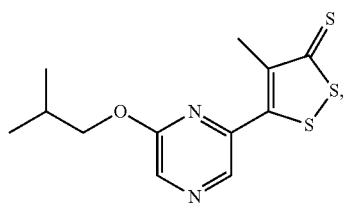

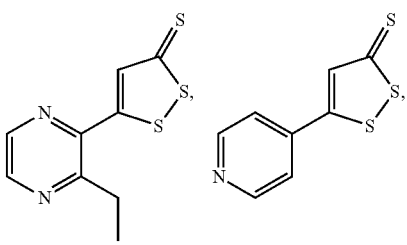

-continued

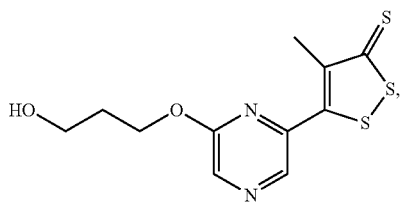

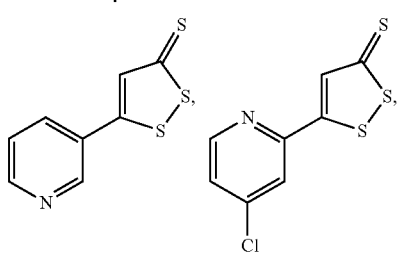

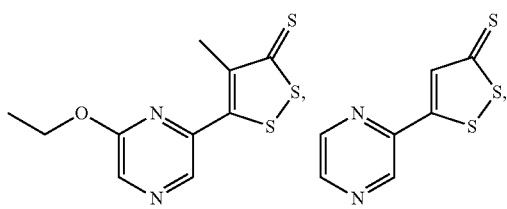

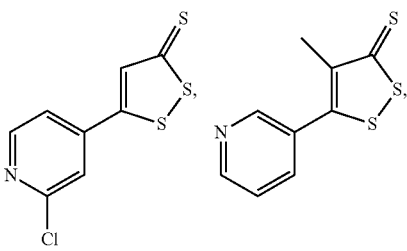

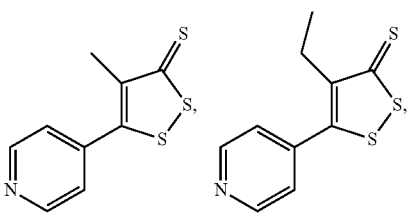

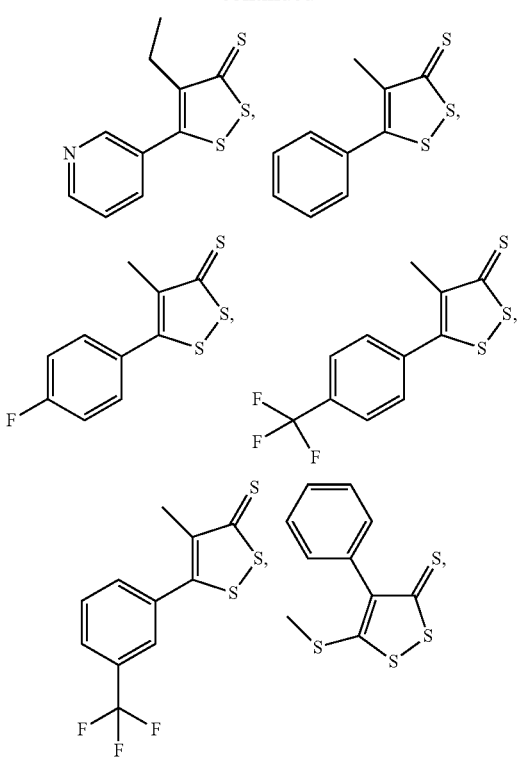

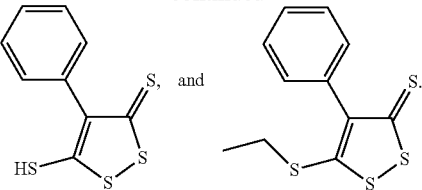

2. A method for treating liver steatosis, comprising administering an effective amount of 4-methyl-5-(2-pyrazinyl)-1,2-dithiol-3-thione, or a pharmaceutically acceptable salt thereof, to a subject in need thereof.

3. The method for treating liver steatosis according to claim 1, wherein the compound or the pharmaceutically acceptable salt thereof is administered at a dose of 1-500 mg in one day.

4. The method for treating liver steatosis according to claim 1, wherein the compound or the pharmaceutically acceptable salt thereof is administered at a dose of 60-120 mg in one day.

5. The method for treating liver steatosis according to claim 2, wherein the compound or the pharmaceutically acceptable salt thereof is administered at a dose of 1-500 mg in one day.

6. The method for treating liver steatosis according to claim 2, wherein the compound or the pharmaceutically acceptable salt thereof is administered at a dose of 60-120 mg in one day.

7. The method for treating liver steatosis according to claim 3, wherein the compound or the pharmaceutically acceptable salt thereof is administered at a dose of 30-200 mg in one day.

8. The method for treating liver steatosis according to claim 5, wherein the compound or the pharmaceutically acceptable salt thereof is administered at a dose of 30-200 mg in one day.

* * * * *

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
tgccatcagc atcttctctg                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
ggctcaccag cttcattagc                                               20

<210> SEQ ID NO 3
<211> LENGTH: 23
<212> TYPE: DNA
<213> ORGANISM: Artificial Sequence
<220> FEATURE:
<223> OTHER INFORMATION: Synthetic construct of LXRE oligonucletide
```

```
<400> SEQUENCE: 3
cagtgaccgc cagtaacccc agc                                    23

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
aacgtcactt ccagctagac                                        20

<210> SEQ ID NO 5
<211> LENGTH: 21
<212> TYPE: DNA
<213> ORGANISM: Artificial Sequence
<220> FEATURE:
<223> OTHER INFORMATION: Synthetic primer

<400> SEQUENCE: 5
ccactaaggt gcctacagag c                                      21
```